(12) United States Patent
Su et al.

(10) Patent No.: US 11,599,851 B2
(45) Date of Patent: Mar. 7, 2023

(54) METHOD FOR REMOTE MANAGEMENT OF THE USING OF CHEMICALS

(71) Applicant: NATIONAL TAIWAN UNIVERSITY OF SCIENCE AND TECHNOLOGY, Taipei (TW)

(72) Inventors: Wei-Nien Su, Taipei (TW); Yu-Cheng Chang, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 0 days.

(21) Appl. No.: 17/015,116

(22) Filed: Sep. 9, 2020

(65) Prior Publication Data

US 2021/0342771 A1 Nov. 4, 2021

(30) Foreign Application Priority Data

Apr. 30, 2020 (TW) .................................. 109114635

(51) Int. Cl.
| | |
|---|---|
| *G06Q 10/08* | (2012.01) |
| *G06K 7/10* | (2006.01) |
| *H04L 67/125* | (2022.01) |
| *G01G 23/42* | (2006.01) |
| *G16H 40/20* | (2018.01) |
| *G06Q 10/087* | (2023.01) |

(52) U.S. Cl.
CPC .......... *G06Q 10/087* (2013.01); *G01G 23/42* (2013.01); *G06K 7/10297* (2013.01); *G16H 40/20* (2018.01); *H04L 67/125* (2013.01)

(58) Field of Classification Search
None
See application file for complete search history.

(56) References Cited

U.S. PATENT DOCUMENTS

| | | | | |
|---|---|---|---|---|
| 2010/0141383 | A1* | 6/2010 | Sano | G01G 19/415 340/5.91 |
| 2014/0315162 | A1* | 10/2014 | Ehrenkranz | G16H 20/60 434/127 |
| 2017/0328764 | A1* | 11/2017 | Tsai | G01G 19/415 |
| 2020/0124465 | A1* | 4/2020 | Carraway | G01G 23/3735 |

* cited by examiner

*Primary Examiner* — Ariel J Yu
(74) *Attorney, Agent, or Firm* — Bacon & Thomas, PLLC

(57) ABSTRACT

A method is performed by using a master smart scale with a master-slave mode, a remote communication device and a slave smart scale to manage multiple chemicals from a remote place. The master smart scale performs an initialization procedure to obtain an initial weight of one chemical; generate an identification information by reading a radio frequency tag of the chemical; use the identification information to inform the remote communication device to open an input page for users to input a basic information into the master smart scale; and mark the basic information and the initial weight with the identification information. In the master-slave mode, the master smart scale allows receiving the information of the chemical from its slave smart scale. For inquiry, a specific page is opened with the remote communication device to receive and display a statistical data generated from the master smart scale.

7 Claims, 2 Drawing Sheets

I. Initializing

II. Using

III. Inquiring

METHOD FOR REMOTE MANAGEMENT OF THE USING OF CHEMICALS

BACKGROUND OF THE INVENTION

(1) Field of the Invention

The present invention relates to a method for managing multiple chemicals, in particular, to a method for remote management of the using of the chemicals in a laboratory or a hospital dispensary by using a smart scale.

(2) Description of the Prior Art

Many chemicals including medicines and drugs are used in the chemistry, material laboratories or in the hospital dispensary. Usually, the chemicals cannot be used up all at once, so the number and variety of the chemicals may increase with time. That will make it difficult for users to manage the exact number and variety of chemicals in the cabinet, the remaining weight of each of the chemicals, or to confirm whether they need to order new products in time, or whether the chemicals have exceeded their shelf life. In addition, there may be many different users for the same chemical in the laboratories or dispensary. From the perspective of managers, it is also very desirable to know whether there is any abnormal using when the chemicals are used by different users.

The users can greatly improve the experiment process, accuracy and safety if they can accurately record the date of use, the number of times of weighing chemicals, the weighing frequency and the weight measured each time, and then combined with the basic information and MSDS safety information of the chemicals. From the perspective of suppliers, if they can understand the use habits of users in real-time, they can provide a renewal delivery and a consumer experience in a timely manner. At the same time, they can also make their own inventory management and logistics more economical and more efficient. In addition, for some special, environmentally safe or expensive drugs, if they can get the daily use information, it will also be of great help to the management efficiency.

However, to manage the chemicals in the laboratory, it is difficult to follow the material management technology used in general supermarkets or warehouses. Most of them first store the information on the barcode or radio frequency tag (also referred to as "RFID tag") of the products, and set the corresponding scanner or reader on the smart scale. The scanner or reader reads the product information as weighing, and returns the scaled weight to the radio frequency tag, or stores the scaled weight and the product information together in an external or cloud storage device. In supermarkets or warehouses, the weight of product is generally constant, so it is usually a one-time weighing of a single product before entering and leaving the shelf/warehouse. However, when one chemical are used in the laboratory, the chemical in the same bottle has a different used amount after each use, so the remaining weight of the chemical is not a steady decrease. Therefore, it is necessary to weigh the remaining weight of the chemical in the same bottle after each use.

At present, some smart scales can be used to weigh and record the remaining weight of the chemical in the same bottle after each use. However, if the user wants to know the using states like the remaining weight of every chemical, he must stay in the laboratory for a long time, to take out each of the chemicals, read the remaining weight of each with the smart scale, record these remaining weights and make a calculation manually base on the recorded remaining weights to obtain a statistical information. It is very time-consuming and it is impossible to calculate and update the using states of all chemicals in real time.

In view of this, the inventors of the present application have improved the conventional management method of chemicals so that the managers and users can inquire in real time or track at the same time the using states of multiple chemicals from different places.

SUMMARY OF THE INVENTION

One object of the present invention is to provide a method for remote management of the using of chemicals, wherein the method is capable of allowing different people to inquire in real time or track at the same time the using states of multiple chemicals from different places, and applied to the situations that the manager may not be in the laboratory or that different chemicals may be scattered in different laboratories.

In order to achieve the aforementioned object, the present invention provides a method for remote management of using of chemicals, used to manage a plurality of chemicals in a laboratory, wherein each of the chemicals is packed in at least one container attached with a radio frequency tag. The method comprises steps of: providing a master smart scale with a master-slave mode, a slave smart scale and a remote communication device, wherein the master smart scale comprises a micro server and a statistical module, and the slave smart scale has a microcontroller for communicating with the master smart scale in the master-slave mode, wherein the micro server has a database and is capable of communicating with the remote communication device via an internet; subsequently, performing an initialization procedure by the master smart scale reading the radio frequency tag on one of the chemicals for the first time to generate an identification information, weighing the one of the chemicals to generate an initial weight and writing the initial weight into the database; the micro server informing the remote communication device to open an input page for plural different users to input a basic information of the one of the chemicals into the database as the master smart scale generates the identification information; and the master smart scale using the identification information to mark the basic information and the initial weight that are stored in the database; after performing the initialization procedure, selecting one of the master smart scale and the slave smart scale in the master-slave mode to read the radio frequency tag for generation of the identification information, and weigh the one of the chemicals after each use to obtain a remaining weight; if the identification information is generated by the slave smart scale, transmitting the identification information from the slave smart scale to the master smart scale to confirm whether both of the basic information and the initial weight exist in the database or not; storing the remaining weight into the database through the slave smart scale for the master smart scale to generate a use record if both of the basic information and the initial weight exist in the database; opening a specific page with the remote communication device to start the statistical module for performing a statistical operation based on the initial weight and the use record that are stored in the database to obtain a statistical data; and transmitting both of the statistical data and the basic information into the specific page through the micro server.

In an embodiment, the micro server comprises a Raspberry Pi, and the remote communication device is a smart phone.

In an embodiment, the use record includes a user name, a weighing time and the remaining weight of the one of the chemicals. The statistical module calculates a use frequency of the one of the chemicals according to the weighing time.

In an embodiment, the one of the chemicals is packed in plural different containers respectively attached with plural radio frequency tags corresponding to plural different items of identification information, and the basic information includes a chemical name, a date of purchase, and a manufacturer. The statistical module searches for and counts the different items of identification information according to the chemical name, to obtain the number of the containers of the one of the chemicals.

In an embodiment, the statistical module calculates a used amount of the one of the chemicals within a specific period for each of the different users according to the chemical name, the user name, the weighing time, the initial weight and the remaining weight.

In an embodiment, a name of the slave smart scale is set into the master smart scale in the master-slave mode for the master smart scale to recognize the slave smart scale, so as to allow the slave smart scale to communicate with the master smart scale.

In an embodiment, if the master-slave mode is turned off, the master smart scale and the slave smart scale each operate independently, so that each stores the remaining weight weighed by itself and the identification information read by itself.

The master smart scale of the present invention can provide a master-slave mode for communicating with the remote communication device through the micro server and the statistical module. For the chemicals scattered in different places, it is more convenient to obtain use records and form the statistical data for real-time inquiry by managers in remote place, and is not limited to the number of people inquiring at the same time and the locations of the chemicals or the inquirers.

DESCRIPTION OF THE PREFERRED EMBODIMENTS

Regarding technical contents, features and effects disclosed above and other technical contents, features and effects of the present invention will be clearly presented and manifested in the following detailed description of the exemplary preferred embodiments with reference to the accompanying drawings which form a part hereof.

Figure 1:
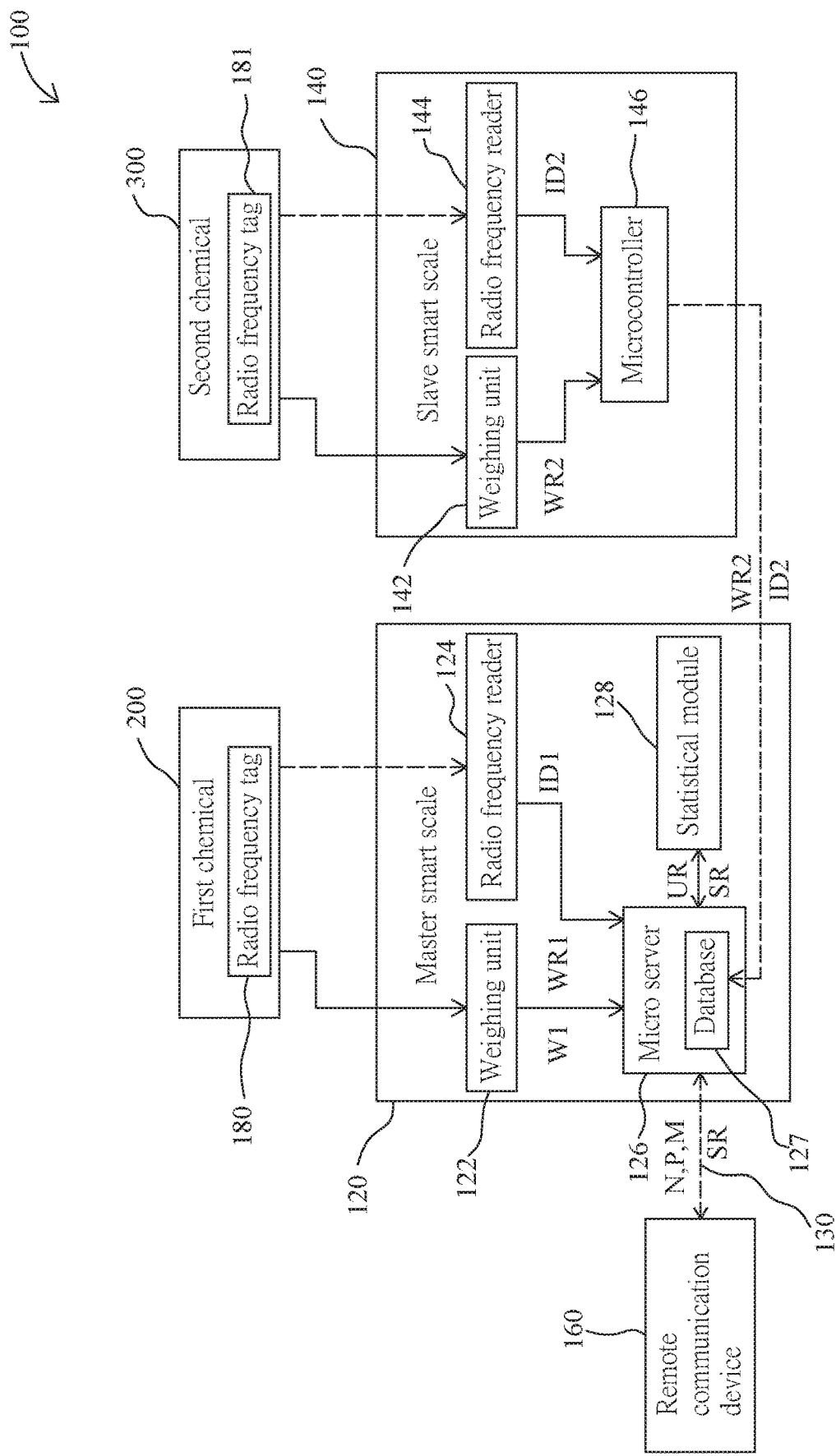
FIG. 1 is the schematic view of one embodiment for a remote management system of chemicals according to the present invention.

FIG. 1 is a remote management system 100 with a master-slave architecture for performing a method for remote management of the using of chemicals according to the present invention. The remote management system 100 includes a master smart scale 120, at least one slave smart scale 140, a remote communication device 160, and radio frequency tags 180, 181 respectively attached to multiple chemicals 200, 300. The master smart scale 120 provides a master-slave mode for communicating with the slave smart scale 140 in the master-slave mode. The master smart scale 120 includes a weighing unit 122, a radio frequency reader 124, a micro server 126 and a statistical module 128. The weighing unit 122 is used for weighing the chemical 200 to generate a weight data, such as an initial weight W1 before the first use or a remaining weight WR1 after each use. The radio frequency reader 124 is used to read the radio frequency tag 180 attached on a container of the chemical 200 to generate an identification information ID1.

The micro server 126 including a database 127 may be referred to as a mini-computer, which is capable of communicating with the remote communication device 160 via the Internet 130. In the embodiment, the micro server 126 receives multiple items of information including the weight data from the weighing unit 122, the identification information ID1 generated by the radio frequency reader 124, a statistical data SR generated by the statistical module 128, and the information and the weight data that are transmitted from outside the master smart scale 120 by the remote communication device 160 or the slave smart scale 140. Furthermore, the micro server 126 transmits the statistical data SR to the remote communication device 160.

The slave smart scale 140 includes a weighing unit 142, a radio frequency reader 144, and a microcontroller 146. The weighing unit 142 is used for weighing another chemical 300 to obtain a remaining weight WR2. The radio frequency reader 144 reads the radio frequency tag 181 of the chemical 300 to correspondingly generate an identification information ID2. If the master smart scale 120 performs an initialization procedure for the chemical 300 to make the identification information ID2 of the chemical 300 stored in the database 127, then the microcontroller 146 of the slave smart scale 140 can communicate with the micro server 126 via the Internet after the master smart scale 120 enables the master-slave mode, so as to transmit the remaining weight WR2 and the identification information ID2 from the slave smart scale 140 to the database 127 for storing them into. While the master-slave mode is turned off, the master smart scale 120 and the slave smart scale 140 each operate independently, and store the weight data and the identification information obtained by themselves in their own memory. As switching to the master-slave mode, the slave smart scale 140 is allowed transmitting the identification information ID2 to the master smart scale 120 to confirm whether both of the basic information and the initial weight of the chemical 300 exist in the database 127 or not.

The remote communication device 160 has a display unit to display an input page for users to input the data into the database 127, and to display the statistical data SR generated from the statistical module 128 when the users make inquiries about.

The master smart scale 120 can receive the basic information of chemicals 200 and 300 entered by the remote communication device 160, and the identification information ID1, ID2 and the use record UR that are generated from the master smart scale itself 120 and the slave smart scale 140. Wherein the basic information, such as the chemical name N, the date of purchase P and the manufacturer M, are usually printed or attached on the containers like bottles or gallipot of the chemicals 200 and 300. On the other hand, the statistical module 128 performs a statistical operation to generate the statistical data SR based on the basic information, the identification information ID1, ID2 and the use record UR, and transmits the statistical data SR from the master smart scale 120 to the remote communication device 160. In this way, the supplier or manager can instantly know the remaining weights WR1, WR2 of the chemicals 200, 300 in the laboratory through the remote communication device 160 such as a mobile device or a computer, so as to solve the problem of the conventional technology.

Figure 2:
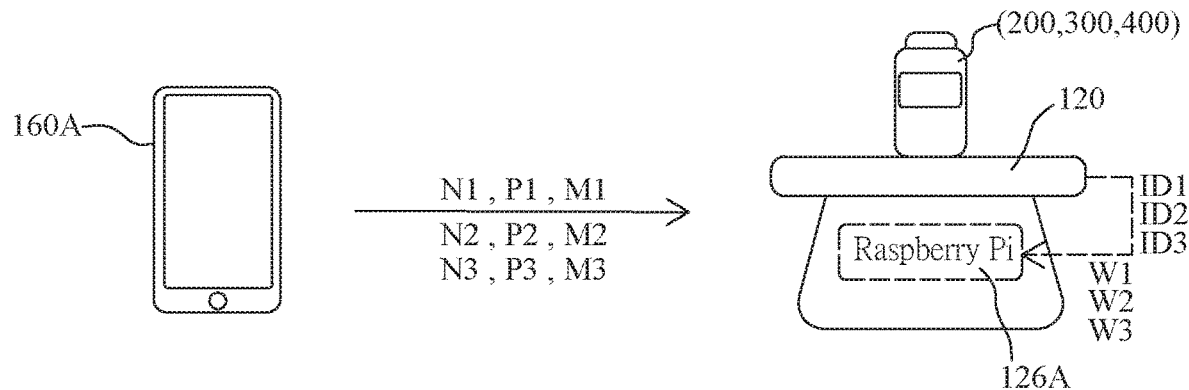
FIG. 2 is the schematic view of one embodiment for a method for remote management of the using of chemicals according to the present invention.
Figure 2:
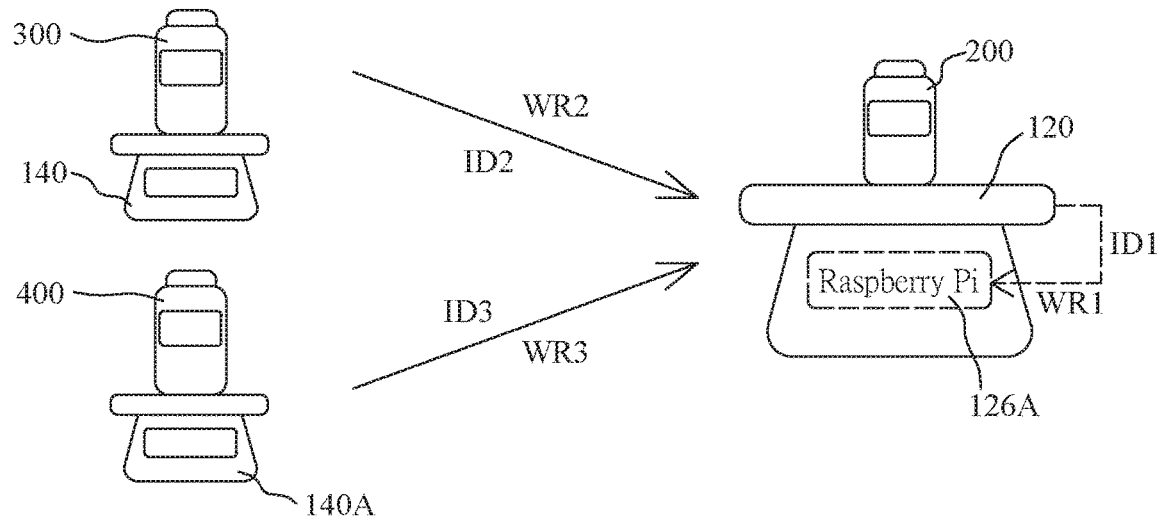
Figure 2:
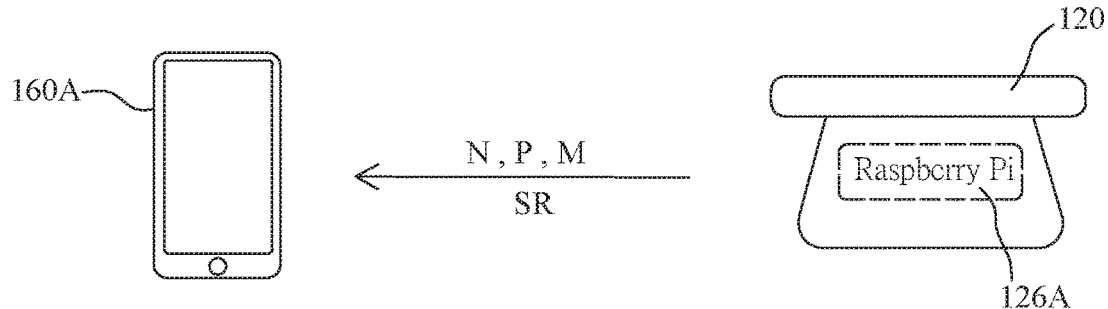

FIG. 2 is a method for remote management of the using of chemicals according to an embodiment of the present invention, which uses the remote management system 100 as shown in FIG. 1 to manage multiple chemicals 200, 300, 400 in a laboratory. The container of each of the chemicals 200, 300, 400 has a radio frequency tag attached on. The micro server 126 of the embodiment is a Raspberry Pi 126A. The database 127 is disposed on the Raspberry Pi 126A. The remote communication device 160 is a smart phone 160A. In the master-slave mode, the names of the slave smart scales 140, 140A are set into the master smart scale 120, so that the master smart scale 120 can recognize the slave smart scale 140 and allow receiving the information from the slave smart scales 140, 140A.

Before each of the chemicals 200, 300, 400 is used for the first time, the master smart scale 120 is used to perform an initialization procedure for each of them. The initialization procedure includes steps as follows. The master smart scale 120 reads the radio frequency tags of the chemicals 200, 300 and 400 to respectively generate the identification information ID1, ID2, ID3 for the first time, weighs the chemicals 200, 300 and 400 to respectively obtain the initial weights W1, W2, W3 of them, and writes the initial weights W1, W2, W3 into the database 127 in itself. As the master smart scale 120 generates the identification information ID1, ID2, ID3 of the chemicals 200, 300 and 400 for the first time, the micro server 126 informs the remote communication device 160 to open an input page. For example, the micro server 126 generates a blank input page marked with the identification information ID1, ID2 or ID3 to transmit to the remote communication device 160 for the opening of the blank input page. Users can use the blank input page to enter the basic information of the chemicals 200, 300 and 400, such as the chemical names N1, N2 and N3 of the chemicals 200, 300 and 400, the date of purchase P1, P2, P3, and the manufacturer M1, M2, M3 into the database 127. And, the master smart scale 120 uses the identification information ID1, ID2 and ID3 to mark the basic information and the initial weights W1, W2, W3 that are stored in the database 127.

After the user completes the initialization procedure for each of the chemicals 200, 300, and 400 with the master smart scale 120, he can select one from the master smart scale 120 and the slave smart scales 140, 140A in the master-slave mode to read the radio frequency tags of the chemicals 200, 300, 400 for respectively generating the identification information ID1, ID2, ID3, and to weigh the chemicals 200, 300, 400 at the same time to obtain the remaining weights WR1, WR2, WR3. At this time, the master smart scale 120 confirms whether both of the basic information of the chemical 200 and the initial weight W1 exist in the database 127 according to the identification information ID1 generated by itself. If so, the remaining weight WR1 is stored in the database 127. The slave smart scales 140, 140A transmit the identification information ID2, ID3 to the master smart scale 120, and confirm whether the basic information of the chemicals 300, 400 and the initial weight W2, W3 exist in the database 127. As the slave smart scales 140, 140A confirm that the basic information of the chemicals 300, 400 and the initial weight W2, W3 exist in the database 127, the slave smart scales 140, 140A transmit directly the remaining weight WR2, WR3 to the database 127 for storing into. Through the above process, the master smart scale 120 can collect multiple items of information about the chemicals 200, 300, 400 to generate their use records UR.

In the embodiment, all steps of the initialization procedure must be executed by the master smart scale 120. The slave smart scale 140 cannot execute the initialization procedure. The function of the slave smart scales 140, 140A is only to read the radio frequency tags on the containers of the chemicals 300 and 400, weigh the chemicals 300, 400 to obtain the remaining weights WR2, WR3, and send the remaining weight WR2, WR3 to the database 127 of the master smart scale 120.

It is worth noting that as the master-slave mode is turned off, each of the master smart scale 120 and the slave smart scales 140, 140A operates independently and stores the information obtained by itself such as the initial weights W2, W3, the remaining weights WR2, WR3 and the identification information ID2, ID3 into its own memory. After switching to the master-slave mode, the slave smart scales 140 and 140A need to confirm whether the initial information, such as the identification information ID2, ID3, the initial weights W2, W3 and the basic information of chemicals 300 or 400, exists in the database 127 or not, and then decide whether to store the remaining weight WR2, WR3 in the database 127 according to the previous confirmation. In other words, the master smart scale 120 must first complete the initialization procedure for each of the chemicals 300, 400, and then the slave smart scales 140, 140A can be allowed storing the remaining weight WR2, WR3 into the database 127.

When users want to make an inquiry about the using of the chemicals 200, 300 and 400, he can use the smart phone 160A to open a specific page, such as a webpage or an application programming interface, to enable the statistical module 128 for performing a statistical operation according to the initial weights W1, W2, W3 and the use records UR in the database 127, so as to generate a statistical data SR of a single or multiple chemicals 200, 300, 400. Through the Raspberry Pi 126A, the statistical data SR and the basic information of the chemicals 200, 300, 400 are transmitted to the specific page.

In one embodiment, the aforementioned use record UR includes the user name, the weighing time and the remaining weight WR1, WR2, WR3 of the chemicals 200, 300, 400. The basic information includes the chemical names N1, N2, N3 of the chemicals 200, 300, and 400, the date of purchase P1, P2, P3 and the manufacturer M1, M2, M3. The statistical module 128 inside the master smart scale 120 can calculate the number or frequency of use of the chemicals 200, 300, 400 according to the weighing time of the chemicals 200, 300, 400. The same one chemical 200, 300 or 400 may be packed in plural different containers respectively attached with plural radio frequency tags, and the radio frequency tags respectively correspond to plural different items of identification information. Take a single chemical 200 as an example, the statistical module 128 counts the number of the containers of the chemical 200 in the laboratory by searching for and counting the different items of identification information respectively corresponding to different containers according to the chemical name N1 of the chemical 200. In addition, the statistical module 128 can also calculate a used amount of the chemical 200 within a specific period for each of different users according to the chemical name N1, the user names, plural items of weighing time, the initial weight W1 and plural remaining weights.

According to the method of the present invention, the user of the chemicals only needs to put the chemicals on the scale to record the weight after each use before put it back into the cabinet, the administrator can know the using states of the chemicals in the laboratory through the remote mobile device or computer. In this way, the user can accurately record the date of use, the number of times of weighing chemicals, the weighing frequency and the weight scaled each time, and then combined with the basic information and MSDS safety information of the chemicals. It can also greatly improve the experiment process, accuracy and safety.

In addition, the suppliers of the chemicals can understand the use habits of users in real-time, so they can provide a renewal delivery and a consumer experience in a timely manner. At the same time, they can also make their own inventory management and logistics more economical and more efficient. For some special, environmental safety concerns or expensive drugs, they can get the daily use information, which is of great help to the overall management benefit.

The conventional technology cannot perform a remote management of chemicals and does not have a master-slave mode. It is difficult to cope with the situation that different chemicals may be scattered in different laboratories. Compared with the conventional technology, the method of the present invention allows different people to query in real time or track at the same time the using states of multiple chemicals from different places, and can cope with the situations such as the manager may not be in the laboratory or different chemicals may be scattered in different laboratories. With the method of the present invention, the user only needs to weigh the chemical after each use, and can efficiently carry out the remote management of a variety of chemicals. There is no need to take out one by one container to know if there are any remaining chemical in it. In addition, the conventional technology generally activates the warning for a single chemical when the chemical is taken out and weighed. However, if the warning function is added based on the method of the present invention, warning messages for multiple chemicals can be sent at the same time. Since the network server of the present invention is built in the master smart scale, and there is no physical connection between the master smart scale, the slave smart scale and the remote communication device, if the system needs to be reset in case of laboratory relocation, it can be more convenient and faster.

The foregoing descriptions of the preferred embodiments of the present invention have been provided for the purposes of illustration and explanations. It is not intended to be exclusive or to confine the invention to the precise form or to the disclosed exemplary embodiments. Accordingly, the foregoing descriptions should be regarded as illustrative rather than restrictive. Obviously, many modifications and variations will be apparent to professionals skilled in this art. The embodiments are chosen and described in order to best explain the principles of the invention and its best mode for practical applications, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary to confine the scope defined by the claims to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules on the requirement of an abstract for the purpose of conducting survey on patent documents, and should not be used to interpret or limit the scope or meaning of the claims. Any advantages and benefits described hereto may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A method for remote management of the using of chemicals, used to manage a remaining amount of a plurality of chemicals selected from a group consisting of drugs and reagents for experiments, the method comprising steps of:

providing a master smart scale, a slave smart scale and a remote communication device;

disposing a micro server inside the master smart scale to communicate with the slave smart scale and the remote communication device, wherein the micro server has a database therein;

generating an identification information and an initial weight for one of the chemicals through the master smart scale, wherein the initial weight is a total weight of a container and the one of the chemicals packed in the container; and employing the micro server to execute following steps of:

providing a blank input page and then marking the blank input page with the identification information through the micro server to form a marked blank input page to transmit to the remote communication device;

receiving a basic information inputted into the marked blank input page after the remote communication device opens the marked blank input page, so as to store the basic information into the database; and marking the basic information and the initial weight with the identification information through the master smart scale to form a marked basic information and a marked initial weight inside the database; and allowing a remaining weight of the one of the chemicals generated from the slave smart scale to transmit to the database for the master smart scale to generate an use record after the slave smart scale confirms that the marked initial weight and the marked basic information exist in the database;

sending warning messages for the plurality of chemicals at the same time when the plurality of chemicals are taken out and weighed; and allowing different users to query in real time and track at the same time the using of the plurality of chemicals scattered in different laboratories.

2. The method according to claim 1, wherein the micro server comprises a Raspberry Pi.

3. The method according to claim 1, wherein the use record includes a user name, a weighing time and the remaining weight of the one of the chemicals, the method comprising:

calculating a use frequency of the one of the chemicals by a statistical module inside the master smart scale according to a weighing time.

4. The method according to claim 3, wherein the one of the chemicals is packed in plural different containers respectively attached with plural radio frequency tags corresponding to plural different items of identification information, and the basic information includes a chemical name, a date of purchase, and a manufacturer, the method comprising:

searching for and counting the different items of identification information through the statistical module according to the chemical name, to obtain the number of the containers of the one of the chemicals.

5. The method according to claim 4, further comprising:

calculating a used amount of the one of the chemicals within a specific period for each of the different users by the statistical module according to the chemical name, the user name, the weighing time, the initial weight and the remaining weight.

6. The method according to claim 5, further comprising:

setting a name of the slave smart scale into the master smart scale for the master smart scale to recognize the slave smart scale in a master-slave mode, so as to allow the slave smart scale to communicate with the master smart scale.

7. The method according to claim 6, further comprising:

operating the master smart scale and the slave smart scale each independently as the master-slave mode is turned off, so that each stores the remaining weight weighed by itself.

\* \* \* \* \*